United States Patent
Dischler

(10) Patent No.: US 11,317,646 B2
(45) Date of Patent: May 3, 2022

(54) METHODS AND COMPOSITIONS FOR RAPIDLY DECREASING EPIGENETIC AGE AND RESTORATION OF MORE YOUTHFUL FUNCTION

(71) Applicant: Louis Dischler, Spartanburg, SC (US)

(72) Inventor: Louis Dischler, Spartanburg, SC (US)

(*) Notice: Subject to any disclaimer, the term of this patent is extended or adjusted under 35 U.S.C. 154(b) by 408 days.

(21) Appl. No.: 16/540,200

(22) Filed: Aug. 14, 2019

(65) Prior Publication Data

US 2020/0054061 A1 Feb. 20, 2020

Related U.S. Application Data

(60) Provisional application No. 62/719,637, filed on Aug. 18, 2018.

(51) Int. Cl.

| | | |
|---|---|---|
| *A61K 31/20* | (2006.01) | |
| *A61K 31/19* | (2006.01) | |
| *A61K 31/15* | (2006.01) | |
| *A61K 31/015* | (2006.01) | |
| *A23L 33/175* | (2016.01) | |
| *A23L 33/12* | (2016.01) | |
| *A23L 29/00* | (2016.01) | |
| *A61K 31/352* | (2006.01) | |
| *A61K 31/26* | (2006.01) | |
| *A61K 33/44* | (2006.01) | |
| *A61K 31/198* | (2006.01) | |

(52) U.S. Cl.
CPC ........... *A23L 33/175* (2016.08); *A23L 29/035* (2016.08); *A23L 29/055* (2016.08); *A23L 33/12* (2016.08); *A61K 31/198* (2013.01); *A61K 31/20* (2013.01); *A61K 31/26* (2013.01); *A61K 31/352* (2013.01); *A61K 33/44* (2013.01)

(58) Field of Classification Search
CPC ........ A61K 31/20; A61K 31/19; A61K 31/15; A61K 31/015
USPC ................................ 514/558, 562, 638, 765
See application file for complete search history.

(56) References Cited

U.S. PATENT DOCUMENTS

| | | |
|---|---|---|
| 9,682,150 B1 | 6/2017 | Gitterle et al. |
| 10,016,509 B1 | 7/2018 | Elliott et al. |
| 2014/0140985 A1 | 5/2014 | Moussa et al. |
| 2018/0271906 A1 | 9/2018 | Moussa et al. |

OTHER PUBLICATIONS

Beltran-Povea et al., "Role of nitric oxide in the maintenance of pluripotency and regulation of the hypoxia response in stem cells," World Journal of Stem Cells (Apr. 2015) PMID 25914767, p. 606.
Bloom, "Amyloid-β and tau: the trigger and bullet in Alzheimer disease pathogenesis," JAMA Neurology (Apr. 2014) PMID: 24493463, p. 502.
Börger et al., "Mesenchymal Stem/Stromal Cell-Derived Extracellular Vesicles and Their Potential as Novel Immunomodulatory Therapeutic Agents," (Jul. 2017) PMID: 28684664, pp. 2-3.
Cataldo, "Solubility of Fullerenes in Fatty Acids Esters: A New Way to Deliver In Vivo Fullerenes," (2008) ISBN 978-1-4020-6844-7, pp. 326-329.
Chen et al., "mTOR regulation and therapeutic rejuvenation of aging hematopoietic stem cells," Science Signaling (Nov. 2009) PMID: 19934433, p. 4.
Chistyakov et al., "Possible Mechanisms of Fullerene C60 Antioxidant Action," BioMed Research International (2013) PMID: 24222918, p. 3.
Dai et al., "Leucine Promotes Proliferation and Differentiation of Primary Preterm Rat Satellite Cells in Part through mTORC1 Signaling Pathway," Nutrients (May 2015) PMID 26007333, p. 3391.
Edmond, "Essential Polyunsaturated Fatty Acids and the Barrier to the Brain," Journal of Molecular Neuroscience (Apr.-Jun. 2001) PMID: 11478373 pp. 186, 190.
Feng et al., "Dihydromyricetin inhibits microglial activation and neuroinflammation by suppressing NLRP3 inflammasome activation in APP/PS1 transgenic mice," Journal of Alzheimer's Disease (Dec. 2018) PMID: 29869390, p. 1212.
Gebara et al., "Taurine increases hippocampal neurogenesis in aging mice," Stem Cell Research (May 2015) PMID: 25889858, pp. 371-372.
Grossi et al., "The Polyphenol Oleuropein Aglycone Protects TgCRND8 Mice against Aß Plaque Pathology," PLoS One (Aug. 2013) PMID: 23951225 pp. 7-10.
Grymula et al., "Evidence that the population of quiescent bone marrow-residing very small embryonic/epiblast-like stem cells (VSELs) expands in response to neurotoxic treatment," Journal of Cellular and Molecular Medicine (Sep. 2014) PMID: 24895014 p. 1803.
Hao et al., "Fullerene mediates proliferation and cardiomyogenic differentiation of adipose-derived stem cells via modulation of MAPK pathway and cardiac protein expression," International Journal of Nanomedicine (Jan. 2016) PMID: 26848263 p. 269.
Hernández-Benítez et al., "Taurine stimulates proliferation and promotes neurogenesis of mouse adult cultured neural stem/progenitor cells," Stem Cell Research (Jul. 2012) PMID: 22484511, pp. 24-27.
Higuera et al., "Patterns of amino acid metabolism by proliferating human mesenchymal stem cells," Tissue Engineering part A (Mar. 2012) PMID: 21943055, p. 660.

(Continued)

*Primary Examiner* — Raymond J Henley, III

(57) ABSTRACT

Disclosed are methods and compositions of reducing the epigenetic age of mammalian organism, especially an adult human of geriatric age. The methods provide for the proliferation of endogenous stem cells using mitochondrial fusion and a UCP2 blocker or other stimulants; supplying stem cells with nutrition to prevent cell cycle arrest; and removal of senescent somatic cells using senolytic treatments. The proliferation of endogenous neural stem cells after plaque removal for the treatment of Alzheimer's is also disclosed.

12 Claims, 2 Drawing Sheets

(56) References Cited

OTHER PUBLICATIONS

Horvath, "DNA methylation age of human tissues and cell types," Genome Biology (2013) PMID: 24138928, pp. 12-13.

Jang et al., "Nicotinamide-induced mitophagy: event mediated by high NAD+/NADH ratio and SIRT1 protein activation," Journal of Biological Chemistry (Jun. 2012) PMID: 22493485, pp. 19304-19307.

Jazwa et al., "Pharmacological targeting of the transcription factor Nrf2 at the basal ganglia provides disease modifying therapy for experimental parkinsonism," Antioxidants and redox signaling (Jun. 11) PMID: 21254817, pp. 2347, 2349.

Jin et al., "Soluble amyloid beta-protein dimers isolated from Alzheimer cortex directly induce Tau hyperphosphorylation and neuritic degeneration." Proceedings of the National Academy of Sciences (Apr. 2011) PMID: 21421841, p. 5819.

Khacho et al., "Mitochondrial Dynamics Impacts Stem Cell Identity and Fate Decisions by Regulating a Nuclear Transcriptional Program," Cell Stem Cell (Aug. 2016) PMID: 27237737, p. 245.

Kilberg et al., "Influence of Amino Acid Metabolism on Embryonic Stem Cell Function and Differentiation," Advances in Nutrition Jul. 2016) PMID: 27422515, p. 785S.

Kim et al., "AMPK activators: mechanisms of action and physiological activities," Experimental Molecular Medicine (Apr. 2016) PMID: 27034026, pp. 4-5.

Kim et al., "EPPS rescues hippocampus-dependent cognitive deficits in APP/PS1 mice by disaggregation of amyloid-b oligomers and plaques," Nature Communications (Jul. 2015) PMID: 26646366, pp. 1-3.

Kim et al., "Taurine in drinking water recovers learning and memory in the adult APP/PS1 mouse model of Alzheimer's disease," Scientific Reports (Dec. 2014) PMID: 25502280, pp. 1-3.

Knoblich, "Mechanisms of asymmetric stem cell division," Cell (Feb. 2008) PMID: 18295577, pp. 583-585.

Kornasio et al., "β-hydroxy-β-methylbutyrate (HMB) stimulates myogenic cell proliferation, differentiation and survival via the MAPK/ERK and PI3K/Akt pathways," Biochimica et Biophysica Acta (BBA)—Molecular Cell Research (May 2009) PMID: 19211028, pp. 755-757.

Lee, et al., "Methionine restriction and lifespan control," Annals of the New York Academy of Sciences (Jan. 2016) PMID: 26663138, p. 1.

Liu et al., "Nicotinamide forestalls pathology and cognitive decline in Alzheimer mice: evidence for improved neurona bioenergetics and autophagy procession," Neurobiology of Aging (Jun. 2013) PMID: 23273573, pp. 1-4.

Nakagawa et al., "Sodium butyrate induces senescence and inhibits the invasiveness of glioblastoma cells," Oncology Letters (Dec. 2017) PMID: 29434841, pp. 1495, 1499.

Nohara et al., "The important role of caspase-10 in sodium butyrate-induced apoptosis," The Kobe journal of medical science (2017) PMID: 18204303, pp. 265-266.

O'Mealey et al., "Sulforaphane is a Nrf2-independent inhibitor of mitochondrial fission," Redox Biology (Apr. 2017) PMID: 27889639, p. 104.

Obata et al., "Nutritional Control of Stem Cell Division through S-Adenosylmethionine in Drosophila Intestine," Developmental cell (Mar. 2018) PMID: 29587144, p. 741.

Pantano et al., "Oleuropein aglycone and polyphenols from olive mill waste water ameliorate cognitive deficits and neuropathology," British Journal of Clinical Pharmacology (Jan. 2017) PMID: 27131215, pp. 54-55.

Senyilmaz et al., "Regulation of mitochondrial morphology and function by Stearoylation of TfR1," Nature (Sep. 2015) PMID: 26214738, p. 1.

Shiraki et al., "Methionine metabolism regulates maintenance and differentiation of human pluripotent stem cells," Cell Metabolism (May 2014) PMID: 24746804, p. 789.

Shyh-Chang et al., "Influence of threonine metabolism on S-adenosylmethionine and histone methylation," Science (Jan. 2013) PMID: 23118012, p. 1.

Van Winkle et al., "Threonine appears to be essential for proliferation of human as well as mouse embryonic stem cells," Frontiers in Cell and Developmental Biology (May 2014) PMID: 25364725, p. 1.

Venkei et al., "Emerging mechanisms of asymmetric stem cell division," Journal of Cell Biology (Nov. 2018) PMID: 30232100, pp. 3791-3792.

Weidner et al., "Aging of blood can be tracked by DNA methylation changes at just three CpG sites," Genome Biology (Feb. 2014) PMID: 24490752, p. 8.

Xavier, et al., "Tauroursodeoxycholicacid increases neural stem cell pool and neuronal conversion by regulating mitochondria-cell cycle retrograde signaling," Cell Cycle (Nov. 2014) PMID: 25483094, pp. 3513-3514.

Yang et al., "Antioxidative fullerol promotes osteogenesis of human adipose-derived stem cells," International Journal of Nanomedicine (Aug. 2014) PMID: 25187705, p. 4023.

Yousefzadeh et al., "Fisetin is a senotherapeutic that extends health and lifespan," EBioMedicine (Oct. 2018) PMID: 30279143, p. 22.

Zhang et al., "Lithium chloride promotes proliferation of neural stem cells in vitro, possibly by triggering the Wnt signaling pathway," Animal Cells and Systems (Nov. 2018) PMID: 30834157, pp. 4866-4867.

Zhang et al., "The role of mitochondria in stem cell fate and aging," Development (Apr. 2018) PMID: 29654217, pp. 1-2.

Zhang et al., "UCP2 regulates energy metabolism and differentiation potential of human pluripotent stem cells," The Embryo Journal (Nov. 2011) PMID: 22085932, p. 3866.

Zhu et al., "New agents that target senescent cells: the flavone, fisetin, and the BCL-XL inhibitors, A1331852 and A1155463," Aging (Mar. 2017) PMID: 28273655, pp. 957-960.

METHODS AND COMPOSITIONS FOR RAPIDLY DECREASING EPIGENETIC AGE AND RESTORATION OF MORE YOUTHFUL FUNCTION

CROSS-REFERENCE TO RELATED APPLICATIONS

This application claims the benefit under 35 U.S.C. § 119(e) of U.S. Provisional Application Ser. No. 62/719,637, filed Aug. 18, 2018, the content of which is incorporated by reference in its entirety into the present disclosure.

FIELD OF THE INVENTION

The claimed methods and nutritional supplements primarily relate to the reduction of average epigenetic age of an adult human organism and tissues thereof, the treatment of diseases of aging, and the restoration of more youthful function.

BACKGROUND OF THE INVENTION

Numerous putative sources of aging are known. These include mutations of nuclear and mitochondrial DNA; inflammation; glycative cross-linking; the intra and extra cellular accumulation of indigestible materials such as lipofuscin; β-amyloid plaques and p-tau tangles in the brain and the associated decline in memory; muscle atrophy; and the oxidized cholesterol derivatives in atherosclerotic plaques. These contribute to the aging of the entire organism or substantial parts thereof, and many believe that so many disparate sources of aging interact that aging is inevitable.

The shortening of telomeres is often considered another source of aging, but herein is considered to be a calendar or clock that provides cellular expiration dates for an organism that is constantly renewing itself. Without stem cells to replace somatic cells reaching their expiration dates, the organism would enter a Hayflick crisis and die. The Hayflick limit is the number of times somatic cells can divide before reaching senescence, typically 40 to 70 divisions. As this is due to the shortening of telomeres, one currently popular solution to the problem is to extend telomeres with supplements such as astragalus extracts containing cycloastragenol. While this may provide short-term health benefits by delaying the Hayflick crisis, it allows cells to continue aging epigenetically, thus becoming ever more dysfunctional.

Epigenetics is the study of the meta programing that controls the expression of genes, wherein hundreds of human cell types are programed from selected portions of the underlying nuclear DNA (nDNA) that is otherwise identical for all diploid cells. Nuclear DNA is bound to proteins called histones, and the expression of genes is raised or lowered by histone modifications. Histones are primarily modified by methylation, but also by phosphorylation, acetylation, ubiquitylation, and sumoylation. At least eleven types of modifications are presently known. These modifications form the epigenome—the epigenetic code that lies above the nDNA code and modulates its expression. Errors in the epigenome—epimutations that occur far more frequently than mutations in the underlying nDNA it controls—degrade the proper functioning of cells and result in aging. In addition, somatic cells become senescent (suffering irreversible cell cycle arrest) due to telomeric shortening, nDNA mutations and other damage, and even a small percentage of senescent cells are known to have an outsized negative effect on the organism. They create inflammation and can drive neighboring cells into senescence with chemical signals, referred to as the senescence-associated secretory phenotype (SASP). While the body removes senescent cells naturally by apoptosis, with age the number of cells reaching senescence steadily increases while stem cell pools decline and the natural processes of clearance and replacement fail to keep up, beginning a vicious cycle wherein epigenetically old senescent cells accumulate at an accelerating rate.

The human organism has stem cells of several types, with variable potential growth possibilities. During fetal development, totipotent stem cells possess the ability to differentiate into any cell of the body and the placenta. Those disappear after a few cycles of replication, leaving the developing fetus with pluripotent (embryonic) stem cells that can develop into any cell of the body, and finally multipotent (adult) stem cells that have more epigenetic nDNA programing than totipotent or pluripotent cells and thus a reduced ability to differentiate into any cell type. Residual pluripotent stem cells in the adult have recently been discovered. All of these, along with more specialized stem cells like satellite cells are herein collectively called stem cells (SCs) unless otherwise specified, while diploid cells with nDNA epigenetically programed to perform as any of the more than two hundred cell types in the body are called somatic cells.

Stem cells are present in all or nearly all tissues of the mature organism. With aging, however, the active SC populations fall even while the function of somatic cells is degraded by stochastic changes to the epigenome (epimutations) which occur at a rate many times the mutation rate of the underlying nDNA, thus detuning somatic cells to their specific function. The result is ageing and the myriad dysfunctions that entails. History is replete with attempts to turn back the clock, with the earliest written records dating back at least to the Epic of Gilgamesh in 1,800 BC, wherein the apocryphal Gilgamesh finds and loses a plant that is said to restore youth. While no single substance is known that can reverse the biological clock, the present application discloses methods and nutritional compositions for doing just that.

According to a current hypothesis, damage to the epigenetic code is the main cause of aging. Methyl groups define most of the epigenetic pattern, and mutations to this pattern occur relentlessly throughout life, due to various environmental conditions and during mitosis. During replication of nDNA, the positions of methyl groups are transferred from the parent DNA strand to the daughter strand by methyltransferases, which operate with relatively poor fidelity compared to the DNA polymerase that replicates the underlying pattern of DNA bases. Methylation errors result in an inappropriate genetic expression for a given cell type, thereby detuning cells for their assigned purpose and propagating this dysregulation to daughter cells, with the level of dysregulation increasing with each generation.

While the epimutations of most genes are stochastic, some portions of the epigenome have been found that degrade with such regularity that they can serve as an epigenetic clock. Selected methylation sites have been found where the aggregate methylation status correlates well with chronological age. Horvath's clock (PMID: 24138928) is one example, which uses several hundred sites. Weidner's clock (PMID: 24490752) is another that samples just 3 sites. The age obtained from such clocks reflects only an average age of cells from the body or selected tissues thereof, which generally comprises a mix of epigenetically old and young cells. During differentiation, stem cells take on an epigenetic pattern appropriate to a specific cell type with near zero age. Fetal somatic cells have a low epigenetic age that increases rapidly through childhood and then at a slower and generally linear fashion until death. Reversing the epigenetic age of an organism is thus a goal that many seek.

Pluripotent (embryonic) stem cells have recently been found to still exist in the adult. Such cells exist in bone marrow and may supply other tissues via blood circulation. In 2014, Grymula et al. (PMID: 24895014) reported that bone marrow provided a source of very small embryonic-like stem cells (VSELs), which can mobilize and circulate with blood. They proposed that these VSELs serve as a reserve of pluripotent stem cells that can give rise to adult stem cells, thus refilling adult stem cell pools. VSELs apparently escaped discovery due to their exceedingly small size and failure of techniques then in use to properly extract them.

In 2013, Shyh-Chang et al. (PMID: 23118012) reported that the pluripotency of mouse embryonic stem cells critically required only one amino acid: threonine. Human embryonic stem cells were thought to require methionine instead, but in 2014, Van Winkle et al. (PMID: 25364725) reported that human embryonic stem cells also required threonine, though not to the same degree.

The replication of stem cells is orchestrated in part by their mitochondria. Mitochondria are organelles of ancient bacterial origin that provide energy for cells by a series of oxidation-reduction reactions, degrading fatty acids, amino acids, and pyruvate (from glucose) to produce ATP, which is then used by cells as their primary energy source. Mitochondria are present in all human cells except red blood cells. The numbers per cell vary according to the energy needs of particular cell types, but the average cell comprises a thousand or more. The mitochondrial count is in constant flux as mitochondria continuously fission and fuse to form individual units or interconnected thread-like structures within cells. Each mitochondrion typically contains multiple copies of bacterial style DNA loops (mtDNA) that operate outside the nDNA system, but with a good deal of crosstalk. In healthy cells, there is an equilibrium between fission and fusion that serves to mix mitochondrial content during fusion and isolate defective mtDNA during fission so they can be lysosomally degraded. Mitochondrial morphology also serves as a trigger for cellular processes. In 2016, Khacho et al., (PMID: 27237737) hypothesized that an overall fusion state biases stem cells into symmetric proliferation (self-renewal), producing two daughter stem cells, while a fission state biases stem cells into asymmetric differentiation where one daughter cell remains a stem cell and the other becomes a somatic cell. Without intervention, it has been estimated that more than 80% of stem cell replication is asymmetric.

In 2018, Venkei et al. (PMID: 30232100) noted that the mitochondria of dividing stem cells become segregated, with the most dysfunctional mitochondria going to the somatic daughter cells where they can be removed by quality control processes. It is hypothesized herein that mitochondrial fusion prevents this segregation and thereby suppresses asymmetric replication. This would be a direct effect rather than the indirect effect of suppression of ROS via mitochondrial fusion postulated by Khacho, who suggested that elongated mitochondria reduce ROS in neural stem cells, thereby promoting symmetric division. In 2008, Knoblich (PMID: 18295577) taught that *Drosophila* stem cells in contact with other stem cells in a niche primarily replicate asymmetrically. In the elderly, much of the stem cell population in a niche may be senescent or have impaired regenerative capacity, thus a method of overriding asymmetric replication resulting from the presence of neighboring stem cells in a niche would allow the SC niche to be expanded.

Stem cell fate can be manipulated via mitochondrial morphology. These energy producing organelles have inner and outer membranes with numerous pores that allow metabolites and ions to pass in a controlled fashion while creating a proton gradient across the inner membrane that can be likened to a battery or capacitor that employs protons instead of electrons. The return flow of protons across the inner membrane is used to produce adenosine triphosphate (ATP) by the process of oxidative phosphorylation. It is known in the art that mitochondria of stem cells are kept quiescent by channels that allow the proton gradient to discharge without doing useful work, thereby preventing ATP production in favor of glycolysis, which is considerably less efficient. Such channels are created by uncoupling proteins (UCP), commonly numbered UCP1, UCP2, etc., in the order of discovery. Five homologues are known in mammals. The mitochondria of human stem cells have numerous channels formed of three UCP2 molecules joined around an axis that allow a return flow of protons (W) through the inner membrane of mitochondria. This proton leakage maintains SC quiescence and limits reactive oxygen species (ROS) production. In 2011, Zhang et al. (PMID: 22085932) showed that UCP2 expression was up to ten times higher in human pluripotent stem cells than in human fibroblasts. They found that UCP2 was repressed during differentiation, by unknown means.

While the exact geometry and manner of activity of UPC2 channels is not well understood, MNR studies suggest that three molecules are joined along an axis to produce a passageway therebetween that diverges slightly at the ends. The small size suggests that a spherical nanoparticle could block the passage of protons, thereby restoring ATP production, banishing quiescence, and forcing stem cells into proliferation or differentiation.

The use of fullerenes to prolong life was the subject of U.S. patent applications by Moussa et al. (Nos. 20140140985 and 20180271906). It was believed by the inventors that $C_{60}$ dissolved in oil scavenged free radicals to prolong the life of rats. This discovery resulted in several companies beginning to sell this product online. And while some users did experience positive results, these tended to fade with time, and after years of use, some complained that they were worse off than before. It is suggested herein that stimulating stem cell mitochondria with $C_{60}$ without controlling mitochondrial morphology or considering stem cell nutrition will ultimately result in asymmetric differentiation, cell cycle arrest, and depletion of stem cell pools, thus producing a decrease in human longevity rather than an increase. Moussa's rats did not live long enough or receive enough treatments to experience this issue, but those versed in the art recognize that the depletion of functional stem cells is a major source of human aging.

U.S. Pat. No. 9,682,150 to Gitterle, et al. and U.S. Pat. No. 10,016,509 to Elliott, et al. are both directed to combinations of $C_{60}$ with phytonutrients and antioxidants mixed into oils, but neither appreciate that fullerenes can be used to restore stem cell pools.

An interrelated source of cellular aging derives from telomeres. Telomeres shorten and otherwise degrade with age, both due to attack by reactive chemical species and erosion during mitosis. Stem cells produce the enzyme telomerase for restoring telomeric length, but most somatic cells substantially lack this enzyme and thus their ability to replicate fails as the number of replications reaches the Hayflick limit. At this point somatic cells cease dividing and become senescent. While the shortening of telomeres is considered a source of aging by some, it has at least two advantages for the adult human organism: First, it halts the proliferation of tumor cells that do not produce telomerase, and second, it halts the replication of epigenetically old cells that would otherwise populate the organism with cells detuned for their tasks by ever growing numbers of epimutations. Thus rescuing near-senescent cells by lengthening telomers can lower telomeric age while detrimentally increasing epigenetic age. It has been found during the present work that use of telomerase supplements can increase epigenetic age rapidly, as old cells no longer become senescent and thus continue to age epigenetically. While in the short term a user might see health benefits due to the reduced load of senescent cells, this will be a temporary improvement.

It is known by those versed in the art that stem cells may be removed from an organism, stimulated in vitro, then returned to the same organism or to a different one—called autologous or allogeneic transplantation, respectively. Such procedures are difficult, dangerous and expensive. While appropriate in certain instances, such as when bone marrow has been destroyed by chemotherapy, they are not appropriate for general epigenetic age reversal, thus the ancient desire to turn back the clock has remained unmet, until now.

SUMMARY OF THE INVENTION

The disclosed protocols and nutritional supplements provide for expanding stem cell numbers and reducing the epigenetic age of a mammalian organism, especially an adult human, and most especially an adult human of geriatric age. Two linked methods are used, each reducing epigenetic age independently, but synergistic when used together. First, endogenous pools of stem cells are enlarged by a cyclic activation of symmetric replication while driving stem cell mitochondrial morphology to fusion. Second, the population of epigenetically old somatic cells is reduced by senolytic agents (apoptosis promoters of senescent cells), preferably while driving stem cell mitochondrial morphology to fission. Specialized stem cell nutrition is provided in both cases.

It is thus a principle object of some aspects of the present invention to proliferate endogenous stem cells in situ.

Another principle object of some aspects of the present invention is to replace epigenetically old somatic cells with epigenetically young somatic cells derived from stem cells, thereby reducing the average epigenetic age of the organism.

Another object of some aspects of the present invention is to proliferate pluripotent stem cells at a greater rate than other stem cell types.

Another object of some aspects of the present invention is to control mitochondrial morphology between fission and fusion states, whereby the fate of stem cells and somatic cells can be directed.

Another object of some aspects of the present invention is to reduce the population of defective mitochondria in parallel with reducing epigenetic age.

Yet another object of some aspects of the present invention is to improve the memory of those suffering from Alzheimer's and other CNS diseases by stimulating neural stem cell pool expansion.

These together with other objects of the invention and various novel features that characterize the invention are particularized in the claims that form part of this disclosure. For a better understanding of the invention, its advantages and the specific objects attained by its uses, reference should be made to the accompanying drawings and descriptive matter in which preferred embodiments of the invention are illustrated.

BRIEF DESCRIPTION OF THE DRAWINGS

The protocols and nutritive compositions will be better understood and objects other than those set forth above will become apparent when consideration is given to the following detailed descriptions thereof. Such descriptions reference the annexed drawings, wherein.

DETAILED DESCRIPTION OF THE INVENTION

Figure 1:
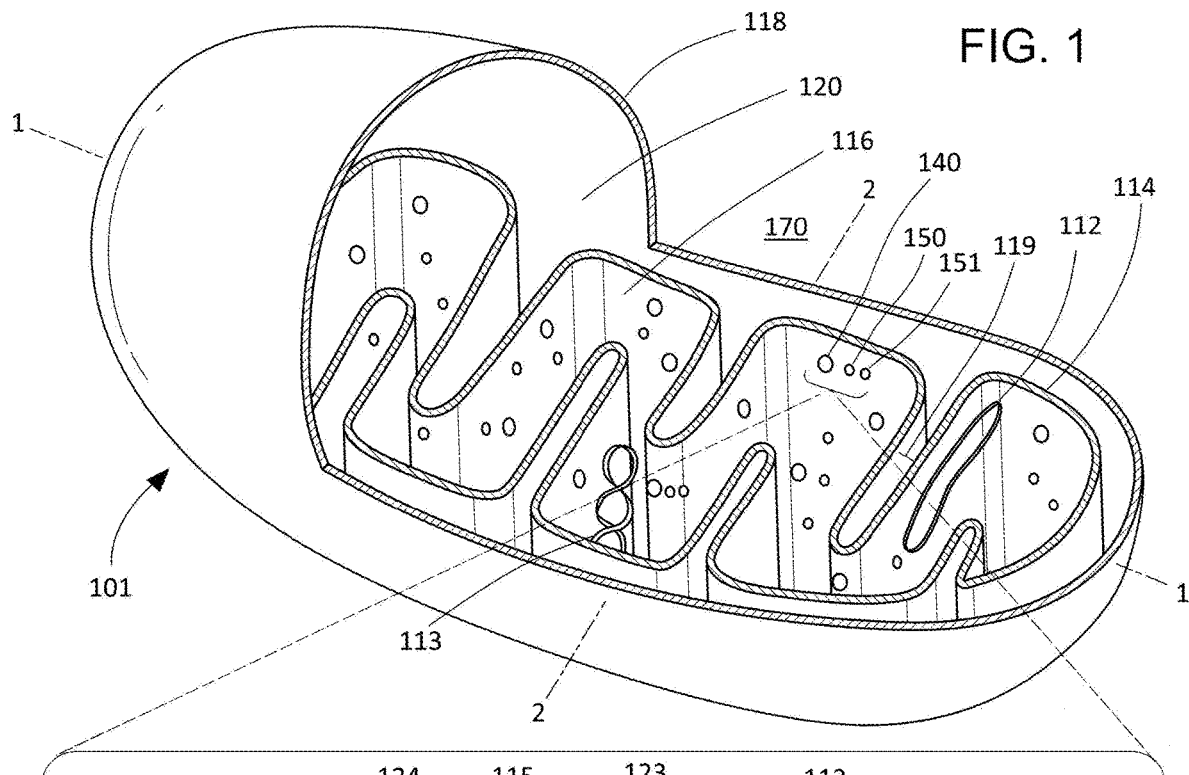
FIG. 1 is an idealized cutaway view of a typical mitochondrion in an intermediate state between fission and fusion.

It is herein argued that aging is primarily an extended Hayflick crisis wherein depleted stem cell pools are unable to replenish growing numbers of cells reaching their telomeric expiration dates, resulting in the increasing epigenetic age of somatic cells and the buildup of senescent cells. By effectively managing this Hayflick crisis, aging can be stopped and even reversed. Disclosed herein is a method for repeatedly stimulating the symmetric proliferation of endogenous stem cells to refill stem cell pools, followed by stimulating the apoptosis of senescent cells, whereby epigenetic age of the organism is reduced and a more youthful state restored.

Preexisting endogenous stem cells are preferred over exogenous stem cells as they are completely compatible with the organism and already distributed widely in tissues. However, endogenous stem cells are not present in sufficient numbers and/or activity to decrease epigenetic age naturally and their numbers decline with chronological age, deficiencies addressed by the methods and nutritive compositions disclosed herein.

Symmetric proliferation (self-renewal) of stem cells is achieved by first supplying stem cells with a mitochondrial fusion promoter, then with a mitochondrial stimulant that blocks proton channels created by mitochondrial uncoupling proteins (UCP2s), or otherwise increases the ATP output of normally quiescent stem cell mitochondria. For some specialized stem cells, signaling molecules may be used to begin proliferation. These steps (which can be performed together or sequentially) are then repeated to increase the numbers of stem cells quasi-exponentially to fill stem cell pools. The population of epigenetically old somatic cells is then reduced by senolytic agents (apoptosis promoters), preferably with somatic cell mitochondria in a fissioned state. Specialized SC nutrition is supplied during SC pool expansion and senescent cell removal. Thus, by replacing epigenetically old senescent cells with epigenetically young cells derived from enlarged SC pools, the epigenetic age of the organism can be reduced at many times the rate of aging. An initial epigenetic age reversal rate of several years per month has been noted with this SC protocol.

Stem Cell Proliferation Stimulants

Stem cells have functional mitochondria, and these mitochondria are kept in a quiescent state by UCP2 channels that allow the passage of protons through the inner membrane without doing useful work, thereby substantially preventing the production of ATP. While not wishing to be bound by theory, it is believed that blocking UCP2 channels will provide the necessary stimulation to begin proliferation. Nanoparticles such as fullerenes can provide such blocking. Fullerenes are preferred due to their generally spherical shape, uniform size, and known predilection for mitochondria, while $C_{60}$ is most preferred as it is the most available, least expensive, and known to be nontoxic. The diameter of $C_{60}$ molecules at 0.7 nm is nearly a million times larger than the proton diameter, but protons in an aqueous environment form hydronium ions ($H_3O^+$), which then cluster with water molecules to form hydrated hydronium. Recent research suggests that the actual ion is $H_{13}O_6^+$. In any case, such water clusters ferrying protons have a significant size that is comparable to $C_{60}$ molecules. Thus when the conical topology at either distal end of UCP2 is blocked by a $C_{60}$ molecule, hydrated hydronium clusters cannot dock or discharge there and the leakage of protons is halted. Mitochondria thus begin generating ATP and quiescence is banished. With mitochondria in a fused state, stem cells are directed to symmetric proliferation and stem cell pools are enlarged.

If molecular size and physical blocking of UCP2 pores are the controlling factors as described, then fullerenes may have quite different chemical properties and still function to stimulate stem cells. In 2014, Yang et al. (PMID: 25187705) showed that the water soluble polyhydroxylated fullerene (fullerol) stimulated osteogenic differentiation of human adipose-derived stem cells, though the mechanism was not understood, while in 2016, Hao et al. (PMID: 26848263) found that $C_{60}$ stimulated brown adipose-derived stem cells. And while the $C_{60}$ in the latter paper was mostly aggregated, some isolated molecules were likely present. Researchers have proposed disparate explanations for this behavior, but herein a more direct action on mitochondria is disclosed, which will become clear when the inner membrane of mitochondria and its pores are examined in detail.

Referring now to the drawings wherein like numerals refer to like parts, FIG. 1 shows a cutaway section of a mitochondrion generally indicated by numeral 101 in an intermediate state between fusion and fission with two bacterial-style loops of mtDNA 112, 113; cytosol 170, the jelly-like fluid in which the mitochondria 101 is embedded; inner mitochondrial membrane 114; matrix 116, a viscid liquid in which oxidative process occur; cristae 119, whereby the surface area of the inner membrane is increased; outer membrane 118; and intermembrane space 120 between inner membrane 114 and outer membrane 118.

If fissioned along axis 2-2, the mitochondrion 101 would be split into two generally spherical mitochondria with each portion containing one loop of mtDNA 112, 113, whereas in a fusion state the mitochondrion 101 would merge with other mitochondria along axis 1-1 and contain many loops of mtDNA. In a state of hyperfusion, it might contain hundreds. In the limit, all mitochondria might be interconnected in threadlike fashion.

Figure 2:
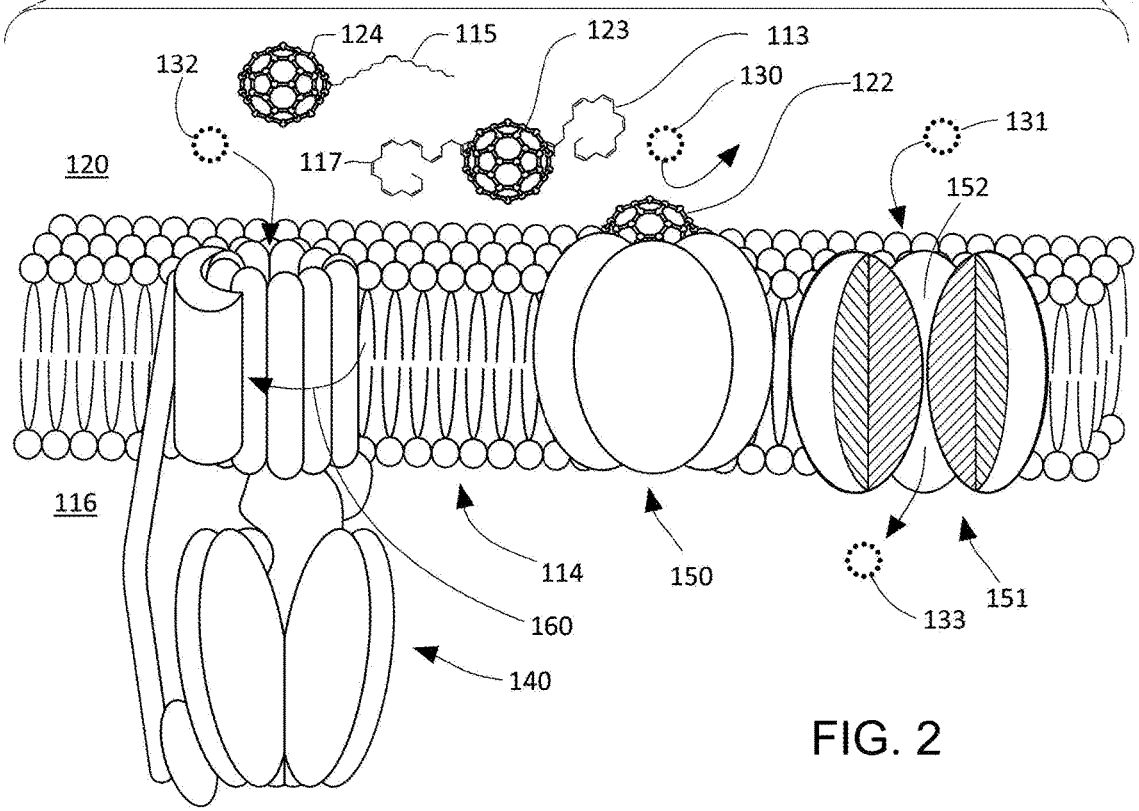
FIG. 2 is an idealized cross-sectional view showing the region around the mitochondrial inner membrane in more detail.

FIG. 2 shows an enlarged cross section of the mitochondrial inner membrane 114, which is approximately 5 nm in wall thickness. Studded in the inner membrane 114 are enzymes ATP synthase 140, which are molecular turbines that channel the return flow of protons derived from hydrated hydronium 132 to mechanically and catalytically convert ADP to ATP. The lower part of ATP synthase 140 extends into the matrix 116 and is static, while the upper portion is buried in the inner membrane 114 and rotates in the direction 160. It has been measured to spin at 130 revolutions per second (7,800 rpm). The lower portion of ATP synthase 140 carries enzymes whereby ADP is converted to ATP.

The inner membrane 114 is also studded with various proteins and enzymes for oxidative processes and for pumping protons from the matrix 116 into the intermembrane space 120. These are well known in the art and are not shown here. In stem cells the inner membrane 114 is also studded with numerous UCP2 channels such as 150 and 151 (the latter shown in cutaway section) that allow protons to bypass ATP synthase 140 and return to the matrix 116 without creating ATP. According to the present hypothesis, molecules of $C_{60}$ 122 (sans adducts), 123 (with eicosapentaenoic acid (EPA) adduct 113 and docosahexaenoic acid (DHA) adduct 117), and 124 (with oleic acid adduct 115), can reversibly block UCP2 channels 150 and 151 to prevent return leakage of protons derived from hydrated hydronium 130, thus temporarily boosting ATP production. UCP2 channel 150 is shown blocked by Cho molecule 122, repelling hydrated hydronium 130.

With UCP2 pores blocked, the surface of the inner membrane 114 facing the inter membrane space 120 will become positively charged in capacitor fashion as protons continue to be pumped from the matrix 116, however, whether protons approach UCP2 pores 150 along the inner membrane 114 surface or via hydronium ions 130, they will be blocked by $C_{60}$ 122, as fullerenes are conductive and thus will become positively charged in contact with the charged inter membrane 114 surface facing the intermembrane space 120. And if $C_{60}$ absorbs protons as Chistyakov et al.'s theoretical work suggested in 2013 (PMID: 24222918), $C_{60}$ 122 would repel like charges even more efficiently.

It appears that Cho molecules 122, 123, 124 cannot dock at the upper distal end of ATP synthase 140 to block the flow of protons carried by hydrated hydronium 132. Such blockers are known, however. One is the antibiotic Oligomycin, which is capable of blocking ATP synthase but not UCP2. As yet unblocked UCP2 pore 151 allows hydrated hydronium 131 (or the proton derived therefrom) to pass down channel 152 where it reappears (or is reconstituted) as hydrated hydronium 133.

With UCP2 pores substantially blocked, the matrix pH rises, increasing the flow of protons through ATP synthase. In somatic cells with few UPC2 channels, this produces a relatively small boost in ATP output, but in stem cells with large numbers of UCP2 channels and thus quiescent mitochondria, this produces a far more dramatic boost, stimulating them into either proliferation or differentiation.

While the actual manner in which UCP2 pores allow proton leakage is not well understood, it is believed that $C_{60}$ shuts down this pathway, and whether that occurs by physically and/or by electrostatically blocking a UCP2 channel thereby preventing conduction of protons (or hydronium), or interfering with protons derived from hydronium transferred to a UCP2 channel, the end result is the same: stem cells are stimulated into an active state in the presence of $C_{60}$ by preventing return leakage of protons to the matrix, thereby increasing ATP output.

Fullerenes dissolved in oils can be delivered orally, and when employed with a SC protocol with a fused mitochondrial morphology, $C_{60}$ has been found efficient at reversing epigenetic age. Olive oil was preferred by Moussa et al., but many other oils may be used. Natural oils have hundreds of components, many yet unknown, and many capable of reacting with $C_{60}$. Thus processed oils are preferred for consistency. Highly refined MCT oils, for example, can dissolve $C_{60}$ while producing few if any adducts. MCT oils are medium chain triglycerides with aliphatic tails of 6-12 carbon atoms, and preferably comprising primarily caproic and/or caprylic acids. MCT oils are readily available and widely consumed. They have lower viscosity and thus more rapidly dissolve $C_{60}$, and are more stable than olive oils. Solution concentrations approaching 0.5 g/L are possible by grinding $C_{60}$ crystals to increase dissolution rate and magnetically stirring at room temperature for a period of approximately 2 weeks, or until substantially dissolved. The actual period is sensitive to the degree of grinding of $C_{60}$ crystals and their purity. The higher the purity the more perfect the crystals, and the more refractory to dissolution. The finished product may then be filtered, but this is considered generally unnecessary. Free fatty acids may also be used, such as oleic acid. Dissolving $C_{60}$ in free fatty acids readily creates adducts, and heating substantially above room temperature results in rapid additions of adducts and rapid dissolution. Much higher concentrations can be obtained in FFAs by heating to a temperature substantially above room temperature, as discussed by Cataldo in 2008 (ISBN: 978-1-4020-6844-7). The resulting formation of adducts has not been found to interfere in stimulating stem cells, though the penetration of the blood brain barrier (BBB) may be sensitive to adduct type. According to Edmond (PMID: 11478373) in 2001, common saturated and monounsaturated fatty acids such as stearic and oleic acids do not enter the brain parenchyma, whereas polyunsaturated fatty acids such as EPA and DHA do.

EXAMPLE

A 5 mg/ml concentration of $C_{60}$ was prepared by stirring in oleic FFA at 75° C. for 3 hours, which is approximately five times the concentration achievable in olive oil and ten times that in MCT oil at room temperature. The whiskey color of the resulting mix resembles the color of $C_{60}$ often achieved in olive oil, suggestive of random oleic acid adducts in both, whereas $C_{60}$ dissolved by stirring in MCT oil at room temperature for two weeks produces the classic purple color of $C_{60}$ solutions in non-reactive solvents such as toluene, suggestive of no adducts. All give results similar in character when taken at the same dosages of $C_{60}$ with a mitochondrial fusion promotor and stem cell nutrition, however $C_{60}$ dissolved in oleic FFA with heat provides effects subjectively stronger than $C_{60}$ dissolved in MCT oil for the same $C_{60}$ content. This may result from more efficient transport of $C_{60}$ with oleic acid adducts into mitochondria.

Fusion and Fission:

Mitochondrial fission and fusion can be achieved with commonly available supplements. For symmetric replication (self-renewal), mitochondrial fusion is stimulated with a fusion promoter. In 2015, Senyilmaz et al. (PMID: 26214738) reported that increased stearic acid (C18:0) intake boosted mitochondrial fusion in flies. In 2017, O'Mealey et al. (PMID: 27889639) reported that sulforaphane caused mitochondrial hyperfusion in cultured cells.

Of the mitochondrial fusion promoters known in the art, stearic acid and sulforaphane are preferred. Those fusion agents most preferred herein comprise stearic acid precursors such as triglycerides with at least one stearic acid moiety, stearic acid diglyceride and stearic acid monoglyceride (glycerol monostearate), and/or a sulforaphane source. These may be conveniently dosed orally, with minimum effective amounts of 500 mg or more for stearic acid as a free fatty acid, and 5-500 mg or more for sulforaphane, with a preferred range of 25-200 mg. Once mitochondrial morphology proceeds to complete fusion, excess stearic acid only serves to produce longer periods of fusion as it is cleared from the body. While stearic acid has a half-life of ten to twelve hours, the fusion state is needed only until stem cells commit to symmetric proliferation. Sulforaphane has a half-life of an hour or more and peaks in the bloodstream in as little as 15 minutes, and may thus be used simultaneously with $C_{60}$. Another agent that acts rapidly is glycerol monostearate, which may be used simultaneously with a UCP2 pore blocker, and can be dispersed in the oil used as a $C_{60}$ solvent for dosing, or dissolved in a hot beverage or food, or intimately mixed with stem cell nutrients to speed absorption. Any substantially nontoxic and digestible source of stearate may be used, though they may have decreasing levels of bioavailability, thus requiring longer digestion times and/or larger doses. These comprise free stearic acid, and glycerol stearates with one to three fatty acid moieties with at least one moiety being stearic acid. Commercial sources of steric acid are generally impure. What is sold as "stearic acid," for instance, are naturally sourced triglycerides that can comprise as much palmitic acid as stearic acid. Nevertheless, they have proven effective in the SC protocols in the amounts stated herein, based on the free fatty acid (FFA) content. Glyceryl stearates are rendered more bioavailable by dispersing them in hot foods, or in such products as cookies and brownies. (Since they melt during baking, they can replace vegetable oil.) Metal soaps such as sodium or magnesium stearate appear to be far less bioavailable. Other fusion promoters (and fission inhibitors) are known and have been used to reduce ischemia/reperfusion injury. One example is mitochondrial fusion promoter M1 (1-(5-Chloro-2-hydroxyphenyl)-ethanone 2-(2,4,6-trichlorophenyl)hydrazone).

The fullerene $C_{60}$ dissolved in triglycerides is presently sold as a health supplement, however such supplements do not contain enough stearic acid to create a state of mitochondrial fusion, and in any case the fusion would come too late, after stem cells have committed to asymmetric replication. $C_{60}$ dissolved in triglycerides has been found to act rapidly, producing an energy boost in thirty minutes or less when taken on an empty stomach, while triglycerides take more than an hour to digest and absorb, thus stearic acid triglycerides are preferably supplied more than an hour before $C_{60}$, more preferably two hours, and most preferably three hours. Glyceryl monostearate and/or steric acid FFAs may be used simultaneously as a unitary dose as they are rapidly absorbed. Due to their high melting points, it is preferred that stearic acid fusion promoters with melting points above body temperature be thoroughly dispersed for immediate availability. They may be mixed in hot foods or beverages, in baked goods, or intimately mixed with amino acids used for SC nutrition, or supplied as a liposomal product, as non-limiting examples.

Another alternative for a unitary dose is to delay the absorption of the fullerene portion by providing a coating to slow dissolution. Enteric coating with fatty acids is one example, but many methods of controlling and delaying drug delivery are well known in the art and may be used here.

For asymmetric replication (differentiation), or to enhance apoptosis, mitochondria are stimulated with a mitochondrial fission (fragmentation) promoter. In 2012, Jang et al. (PMID: 22493485) showed that a high ratio of oxidized to reduced nicotinamide adenine dinucleotide ($NAD^+$/NADH) promotes mitochondrial fission, thus increasing $NAD^+$ will raise that ratio. $NAD^+$ promoters comprise niacin; nicotinamide; nicotinamide riboside (NR); nicotinamide and ribose (N+R); niacin and ribose; nicotinamide mononucleotide; and oxidized nicotinamide adenine dinucleotide. N+R is preferred for low cost, easy availability, and low toxicity. N+R may be conveniently dosed orally, with minimum effective amounts ranging upward from a quarter gram each for nicotinamide and riboside, and preferably a gram of each, and more preferably two grams of each. After mitochondrial fission proceeds to completion, excess promoters only serve to maintain fission until $NAD^+$ is reduced to NADH, thus lowering the $NAD^+$/NADH ratio, or fission is otherwise overridden by supplementation with a fusion promoter.

While a high $NAD^+$/NADH ratio promotes fission, stearic acid in the doses discussed has been found to promote fusion more profoundly, thus the latter overrides the former: e.g., 10 grams of food grade triglyceride comprising approximately 50% stearic acid moieties will override 2 grams each of nicotinamide and ribose. $NAD^+$ can therefore be increased in conjunction with stem cell proliferation, where it works in parallel with the UCP2 pore blocker to increase stem cell mitochondrial activity and thus enhance proliferation. With fusion established by stearic acid, nicotinamide and ribose can be orally dosed an hour or more before the UCP2 pore blocker, while other substances known to raise $NAD^+$ may need to be taken three hours are more before the pore blocker. The majority of a nicotinamide riboside dose, for instance, is believed to be enzymatically broken down in the small intestine before absorption. Thus nicotinamide+ ribose is preferred.

It should be noted that rapid acting mitochondrial fusion promoters can raise blood pressure in some who are already hypertensive, and thus more BP medication may be required before dosing with such fusion agents. In similar fashion, fission promoters can lower BP.

Senescent Cells and Telomeres:

Although stem cells produce telomerase, it is known that this enzyme can nevertheless fail to maintain telomere length. Some may therefore find it desirable to extend telomeres during proliferation from time to time. Telomerase stimulating supplements comprise cycloastragenol and astragalus extracts that are known to contain cycloastragenol and other putative telomerase stimulants. Herein it is generally not desirable that telomeres of somatic cells be extended, as this would allow epigenetic age to increase. Thus telomere stimulating supplements should be used rarely, or not at all.

Senolytic treatments reduce the population of senescent cells more rapidly than natural processes. While senescent cells aren't rendered senescent because of their advanced epigenetic age, they are generally among the epigenetically oldest cells of the body. And while they are cleared naturally, this process can lag with age and with the declining availability of functional stem cells to replace them. In 2017 Zhu et al. (PMID: 28273655) discussed a number of senolytic compounds capable of increasing the natural removal of senescence cells via apoptosis. These include dasatinib, quercetin, navitoclax, piperlongumine, and fisetin.

It is suggested herein that clearance of senescent somatic cells naturally declines when new somatic cells derived from stem cells are not available to replace them, and increases when stem cell pools are filled and healthy. Thus increasing the stem cell pools should enhance senolytic treatments, as should supplying stem cell nutrition during senolytic treatment. Previously the senescence-associated secretory phenotype (SASP) was described whereby senescent cells communicate with nearby cells, increasing inflammation and promoting senescence. Analogously, stem cells secrete extracellular vesicles that create an environment allowing endogenous stem and progenitor cells to successfully repair damaged tissues. This active area of research was reviewed by Borger et al. in 2017 (PMID: 28684664). Given the reparative aid of these vesicles, stem cell pools are best filled before senolytic treatments.

It is estimated that some 50 billion senescent cells are recycled daily by apoptosis. Apoptosis is an orderly form of cellular suicide that is much less toxic to the body than necrosis, though effects can still be perceived. An effective senolytic treatment would necessarily increase the average rate substantially before subjective effects could be easily distinguished over baseline. These effects are often described as flu-like symptoms such as muscle pains and lethargy. In fact, the influenza virus is known to stimulate cellular apoptosis, which is necessary for viral replication. The symptoms produced by senolytic treatments may be reversed with stearic acid, showing that mitochondrial fusion ends apoptosis, thus fusion blockers such as stearic acid and/or sulforaphane should prove useful in interrupting viral pathogenesis, slowing or stopping the exponential growth of virions as immunity is built up. Other widespread viruses that spread by apoptosis and thus might be slowed or stopped by fusion promoters are herpes simplex and HIV. The Ebola virus stimulates massive apoptosis, thus fusion agents might be particularly helpful.

It is known in the art that apoptosis begins with mitochondrial fission, which can be achieved with $NAD^+$ precursors such as N+R and/or apigenin (4',5,7-trihydroxyflavone), as non-limiting examples. A series of cellular enzymes (caspases) are then stimulated by senolytic agents to act in a cascade, driving senescent cells into programed apoptosis.

Of particular use for removing senescent cells are nicotinamide and ribose (N+R) to stimulate fission, along with curcumin (preferably liposomal, or with other enhancement to improve bioavailability) and resveratrol. Curcumin and resveratrol are known to drive certain cell types to senescence, and in 2018 Yousefzadeh et al. (PMID: 30279143), found that curcumin also acted as a senolytic when used alone, and resveratrol to a lesser extent. Herein, they appear to work synergistically with sodium butyrate in removing senescent cells by apoptosis. In 2007, Nohara et al. (PMID: 18204303) showed that sodium butyrate stimulated caspases 3, 8 and 10. Butyrate salts such as sodium, potassium, lithium, calcium, magnesium and mixtures may be used, as nonlimiting examples, though the sodium salt may be less likely to cause digestive problems. When used with other senolytic agents and mitochondrial fission, 200 mg to 10 grams of a butyrate source at intervals of half an hour to two hours for several hours are effective doses, with 500 mg to 1 gram preferred. Glyceryl monobutyrate, glyceryl dibutyrate, and glyceryl tributyrate (tributyrin) may also be used, with the speed of action decreasing in the order listed. Butyrates are commonly used in humans and animals for digestive health.

AMPK (AMP-activated protein kinase) activators may also be used, which are known to promote apoptosis. Curcumin and resveratrol are indirect AMPK activators, while an example of a direct activator is salicylate. As aspirin is rapidly broken down into salicylate, it may be added to a senolytic protocol in the amounts of 100 mg to 2 g. In 2016, Kim et al. (PMID: 27034026) tabulated a number of direct and indirect AMPK activators that might be used here.

Adding stem cell nutrition appears to improve the results of senolytic treatments, likely because stem cells are called upon to replace senescent cells at a rate much higher than normal. Amino acids such as lysine, leucine, methionine, taurine, and threonine may be used. Also useful are the leucine metabolite β-hydroxy-β-methylbutyrate (HMB) and the methionine derivative S-adenosylmethionine (SAMe). Typical effective doses of lysine, HMB, leucine, taurine, and threonine are between 100 mg and 20 grams, and preferably between 1 gram and 10 grams each. For SAMe and Methionine, typical effective doses range between 100 mg to 5 grams. Additionally, glutamine and isoleucine may be used at the 1-5 gram levels. This nutrition may be supplied an hour before or after the senolytic treatment, but most conveniently they are delivered concurrently. For replacement of senescent cells to be effective, pools of stem cells are needed, thus treatments to increase the numbers of stem cells preferably precedes the replacement of senescent cells.

Examples of Nutritional Supplements for Senolytic Treatments:

Senolytic Example 1 (Dose)

Nicotinamide (2 g)
Ribose (2 g)
After one hour—
Curcumin, liposomal or phytosomal (2 g)
Resveratrol (500 mg)
Stem cell nutrition (SC nutrition cocktail example 2, below)
Then at intervals of 30 minutes for 2-4 hours—
Sodium butyrate (500 mg)

Senolytic Example 2 (Dose)

Apigenin (200 mg)
Curcumin, liposomal or phytosomal (2 g)
Resveratrol (500 mg)
Stem cell nutrition (SC nutrition cocktail example 2, below)
Then at intervals of 30 minutes for 2-4 hours—
Sodium butyrate (500 mg)

Satellite Cells:

Satellite cells are skeletal muscle stem cells that maintain muscle mass and contribute to muscle regeneration following injury or damage. The name derives from their location on the periphery of muscle fibers. In children, the fraction of satellite cells is high. With time these cells differentiate, adding their nuclei to muscle tissue. In the adult the ratio of active satellite cells to the underlying muscle cells declines and may become depleted in the elderly. Therefore it is advantageous to increase the ratio via satellite cell self-renewal to restore muscle function to more youthful levels. In 2015, Dai et al. (PMID: 26007333) showed that the amino acid leucine promoted satellite cell differentiation of primary preterm rat satellite cells via upregulation of mTORC1, which promotes growth based on the availability of nutrients. In 2009, Chen et al. (PMID: 19934433) determined that upregulation of mTORC1 depleted hematopoietic stem cell pools, producing accelerated aging. Accordingly, upregulation of mTORC1 might also accelerate satellite cell depletion and produce sarcopenia and accelerated aging. Chen did not consider mitochondrial morphology, however, which when driven to fusion, promotes self-renewal rather than differentiation. Thus the upregulation of mTORC1 along with mitochondrial fusion can build up satellite cell pools and delay or reverse aging rather than accelerate it. Leucine and its metabolite HMB can thus be useful when combined with mitochondrial fusion.

Nitric oxide (NO) is a known stimulant for satellite stem cells and nitric oxide sources are sold for improving exercise performance and vascularization. Combining a nitrate source with a mitochondrial fusion agent can increase proliferation over differentiation and avoid the potential of satellite cell depletion. In 2015, Beltran-Povea (PMID: 25914767) showed that SC's could be stimulated into proliferation by NO, but also into differentiation and apoptosis, depending on concentration. This suggests that higher doses of NO drive mitochondria to fission, as fission is necessary for apoptosis. Driving mitochondria to fusion will bias SCs to proliferation over differentiation or apoptosis. Indeed, inorganic nitrates have been found herein to build muscle more rapidly when used with stearic acid and/or sulforaphane fusion.

In experiments, stearic acid triglyceride (10 grams, 50% stearic acid) was used 2-3 hours before 300 mg of potassium or sodium nitrate. Effective doses of stearic acid triglyceride range from 2 to 30 grams, leucine from 1 g to 30 g, and potassium nitrate from 100 mg to 5 g. More rapid fusion agents may be used for a unitary dose, such as glyceryl monostearate and/or sulforaphane. Doses of 500 mg to 10 g for glyceryl monostearate are effective, or 10 to 500 mg of sulforaphane glucosinolate. Most effective is 1-3 g for glyceryl monostearate and/or 50-100 mg of sulforaphane, taken together with 100 mg to 1 g potassium or sodium nitrate, with 200-500 mg most preferred. Other nitrate sources may be used, with metal salts most preferred for rapid bioavailability. Other non-limiting examples include lithium, magnesium and calcium nitrates.

Stem Cell Fate Modulators:

Apart from the supplements for fusion previously mentioned, other substances can direct cells toward self-renewal. One such substance is tauroursodeoxycholic acid (TUDCA). It was reported in 2014 by Xavier, et al. (PMID: 25483094) that TUDCA is orally available and penetrates the BBB, where it biases neural stem cells to self-renewal and cell cycle progression, and during differentiation biases somatic daughter cells to neuronal rather than glial paths. Thus TUDCA is expected to further increase self-renewal when used with fusion promoters capable of penetrating the BBB, and increase neurogenesis when used with non-fusion or fission mitochondrial states. TUDCA may be most usefully combined with taurine and a fusion promoter. Effective doses range from 50 mg to 20 g, with 100 mg to 10 g preferred, and 250 mg to 1 g most preferred.

Antioxidants for Self-Renewal:

Stem cells are thought to be biased to self-renewal by mitochondrial fusion in part because of lower ROS levels in the fusion state, thus antioxidants can be used to help achieve lower ROS and protect stem cell telomeres from erosion during mitosis. TUDCA mentioned above as a stem cell modulator is also a useful antioxidant. Glutathione is the primary mitochondrial antioxidant and is thus useful in the SC protocol. It is orally available when taken in a liposomal or phytosomal form. Effective doses range from 100 mg to 10 g, more preferably 250 mg to 5 g, and most preferably 500 mg to 2 g.

Stem Cell Nutrition:

Of the stem cell types available in the body to be proliferated, pluripotent stem cells are most desirable as they are the most versatile. They also possess the least epigenetic programing and thus will have the greatest effect in lowering epigenetic age. Threonine is known to be the only amino acid needed for mouse pluripotent SCs, however, it has previously been thought this was not the case for human pluripotent SCs. In 2014, Van Winkle et al. (PMID:

25364725) reported that the amino acid threonine appears to be required for human embryonic (pluripotent) stem cell proliferation as well, though not as a single supplement and only under certain conditions. Methionine is generally recognized as the primary amino acid needed for human pluripotent SCs.

Some adult stem cells are known to require a specific group of nutrients, but it is likely that the nutritional requirements of all stem cell pools are not yet known. In 2014, Kilberg et al. (PMID: 27422515) reported that the amino acid requirements of human embryonic cells (hESCs) in vitro included methionine, lysine and leucine. Absent these amino acids, hESCs entered cell arrest and ultimately progressed to apoptosis. Thus they are included for SC nutrition. To these can be added the metabolic products S-adenosylmethionine (SAMe) derived from methionine, and β-hydroxy-β-methylbutyrate (HMB), derived from leucine. By avoiding cell cycle arrest when suitable nutrients are supplied, fewer cycles of endogenous stem cell treatments are needed.

In 2014, Shiraki et al. (PMID: 24746804) showed that depletion of either methionine or SAM-e reduces proliferation and can result in prolonged cell arrest of pluripotent cells leading to apoptosis. Thus supplementing SAMe with fusion biased self-renewal will further insure that self-renewal is achieved. Effective doses of SAMe in an adult human would range from 5 mg to 5 g, with a preferred range of 50 to 200 mg.

The proliferation of neural stem cells is enhanced by the amino acid taurine. This was shown in aging mice by Gebara et al. (PMID: 25889858) and later in humans during perinatal cortical development. Thus taurine may be used as a nutritive addition, in particular when neural stem cell pools are to be enhanced. This may be used in conjunction with the stem cell modulator and antioxidant TUDCA. Effective doses of taurine in an adult human would range from 500 mg to 50 grams, with a preferred range of 2 to 20 grams. It may also be used as a stem cell stimulant.

In 2012, Higuera et al. (PMID: 21943055) studied the uptake by mesenchymal stem cells of various amino acids and found that the amounts used varied widely according to conditions—whether growing statically on plates or dynamically in a bioreactor, for instance. For a dynamic culture, glutamine, leucine and isoleucine were most used by the SC cultures.

Herein it is expected that in vivo requirements will be different still, and the requirements of different stem cell types will vary, along with individual differences from one human organism to the next, as will the nutrients already available endogenously. In 2016, Kilberg et al. (PMID: 27422515) reported on the wide variability of stem cell requirements, depending on type. They reviewed research showing how the fates of stem cells in vitro can be directed by nutrition. Thus there is likely no one best nutritional cocktail, even for one person, no more than eating the same meal three times a day would be healthy. In fact, use of amino acids that stimulate stem cells may be decidedly unhealthy in the long run when used outside the present SC protocol. The level of methionine in the diet, for instance, is associated with shortened lifespan, and the currently popular calorie restriction diet for longevity has been said to actually amount to methionine restriction. In 2016, Lee et al. (PMID: 26663138) listed a number of pathways whereby methionine restriction might extend lifespan, yet the results are inconsistent and thus unconvincing. As discussed above, methionine depletion can result in pluripotent SC arrest and apoptosis. But when methionine is readily available, pluripotent stem cell activity increases. And without mitochondrial fusion to promote proliferation over differentiation, pluripotent SCs can become depleted over a lifetime of use. With the appropriate addition of mitochondrial fusion to expand reserves of pluripotent SCs, however, it becomes unnecessary to starve oneself to live longer.

The following cocktail of amino acids has been employed. All amounts are for a male subject of about 80 kg:
Examples of Sc Nutritional Supplement Cocktails:

SC Nutritional Cocktail Example 1 (Dose)

Methionine (5 g)
Lysine (2 g)
Leucine (2 g)

SC Nutritional Cocktail Example 2 (Dose)

Taurine (5 g)
Methionine (5 g)
Lysine (2 g)
Leucine (2 g)
Threonine (5 g)
Glutamine (2 g)
Isoleucine (500 mg)
HMB (1 g)
SAMe (500 mg)

In the above nutritional examples, amino acids can be supplied in capsules or tablets, or by dissolving/dispersing in fruit juice or flavored water. Those supplements with poor taste are preferably supplied in liposomal, phytosomal, tablet or capsule form.

Figure 3:
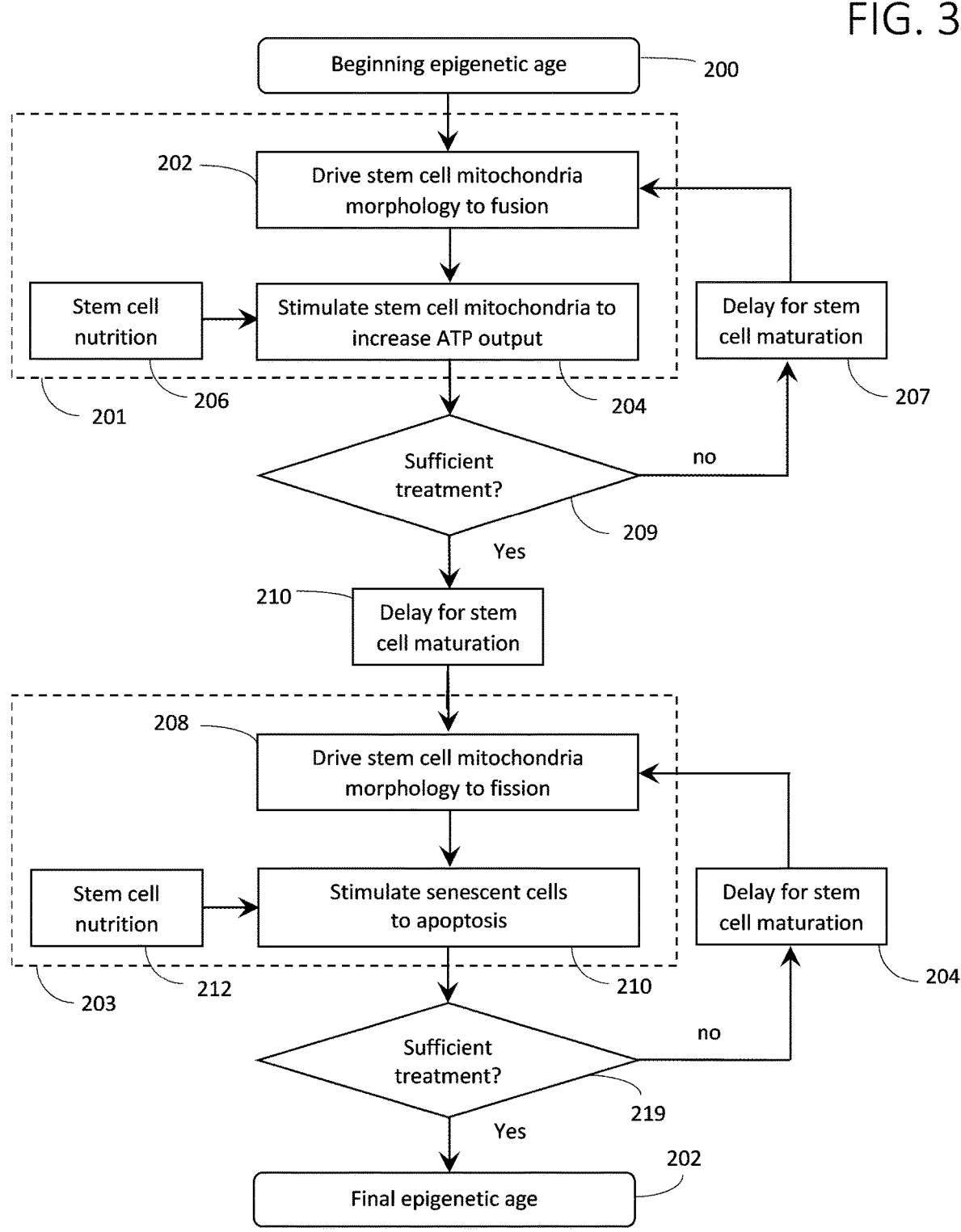
FIG. 3 is a flowchart of the inventive method wherein stem cell pools are filled and senescent cells removed.

Epigenetic Age Reduction Flowchart:

Turning again to the drawings, FIG. 3 shows a flowchart of the inventive method in which a mammalian organism has a beginning epigenetic age 200 before SC replenishment, indicated by dashed box 201. SC replenishment step 201 comprises steps 202, 204, 206. At step 202, stem cells are driven into fusion, and at step 204, stem cells receive nutrition 206 and are stimulated to increase ATP output, thereby beginning proliferation. These steps may be combined in step 201 if a fast-acting fusion supplement is used. If the treatment results are judged insufficient at decision step 209, steps 202, 204 and 206 are repeated after delay step 207. Stem cells are known to require approximately one day to mature (though this varies between types), so to efficiently begin a new cycle, this delay is preferably a day or more. While the number of cycles are a matter of individual judgement, they are preferably greater than one and more preferably at least five, and most preferably at least ten, at least initially.

After sufficient stem cell treatment cycles have been achieved, senolytic treatment step 203 can begin after delay step 221, which is preferably two days or longer. Senolytic treatment step 203 comprises steps 208, 210, 212. At step 208, stem cells are driven into fission, and at step 210, stem cells receive nutrition 212 and senescent cells are stimulated to apoptosis. If the treatment results are judged insufficient at decision step 219, steps 208, 210 and 212 are repeated after delay step 204, which is preferably a day, and more preferably a week or more. Steps 208, 210 and 212 may be combined if a suitable fast acting fission supplement is used, such as apigenin. The number of treatment cycles are at least one and preferably not more than three. Senescent cells are removed and replaced by stem cells produced during repeated steps 202, 204 and 206, producing a final epigenetic age 202 lower than beginning epigenetic age 200.

Epigenetic age will continue to decline for weeks as stem cells with low epigenetic age replenish rapidly dividing transit cells, which in many organs do the bulk of the work in providing the organism with new somatic cells. It is these transit cells that is expected to be most impacted by telomerase supplements, and thus such supplements can rapidly increase average epigenetic age.

Example Protocols for Epigenetic Age Regression:

SC Replenishment (Step 201) Example 1 (Dose)

Stearic acid triglyceride (8-12 g)
After 2-4 hours—
$C_{60}$ in oil (1-5 mg)
Supplements of nutritional cocktail examples 1 or 2

SC Replenishment (Step 201) Example 2 (Dose)

Glycerol monostearate (1-3 g)
$C_{60}$ in oil (1-5 mg)
Supplements of nutritional cocktail examples 1 or 2

Senolytic Treatment (Step 203) Example 1 (Dose)

Nicotinamide (1-2 g)
Ribose (same dose as nicotinamide)
After 1-3 hours—
Curcumin, liposomal or phytosomal (2 g)
Resveratrol (500 mg)
Supplements of nutritional cocktail examples 1 or 2
Then at intervals of 30 minutes for 2-4 hours—
Sodium butyrate (500 mg)

Senolytic Treatment (Step 203) Example 2 (Dose)

Apigenin (100-500 mg).
Curcumin, liposomal or phytosomal (2 g)
Resveratrol (500 mg)
Supplements of nutritional cocktail example 1
Then at intervals of 30 minutes for 2-4 hours—
Sodium butyrate (500 mg)

In the above examples, stearic acid sources can be supplied in baked goods, hot foods, nutritional bars, or any method that enhances digestion. Other senolytics may be substituted for those noted.

Treatment Results:

A male subject, 66 years old and in substantially good health, trialed the stem cell protocol. After 3 months (34 SC replenishment treatments and one senolytic treatment) he found that pain in both knees and joint instability in one knee that had troubled him for years faded and disappeared, as did a needle-like pain in one patella when kneeling. He noted tighter and smoother skin and disappearance of all age wrinkles on face. Most broken capillaries in face disappeared. A skin pinch test (time to recovery after pulling up neck skin with two fingers) went from 3 seconds to 1. He noted greater muscle mass and less fat, and greater stamina. His formerly flat feet developed a noticeable arch. Tenosynovitis in one palm disappeared. A distortion he had seen in the Amsler grid that had remained stable for approximately 15 years also disappeared.

These seemingly unrelated changes are only consistent with systemic stem cell activity.

His epigenetic age also went down sharply, and this effect was much greater than anticipated. Several companies are presently offering epigenetic tests that proport to give epigenetic age. The subject had taken a test offered by Osiris Green two months prior beginning treatment. This company found that epigenetic age can be reliably measured by sampling the methylation patterns of just three gene markers taken from buccal cells (similar to Weidner's clock, which uses 3 markers from blood), with an overall median absolute deviation 1.8 years. The subject's baseline test fell well within that range, with a calculated epigenetic age 0.52 years higher than his chronological age. A second test after the 3-month treatment and 5 months after the baseline test, reported an estimated age more than 11.2 years below his first estimated age. This was far outside the expected range, representing an epigenetic age reduction of approximately 3.7 years per month of treatment.

This subject had previously used $C_{60}$ outside of the protocol and found that initially positive results faded after a year and subsequent use of $C_{60}$ produced no effects at all apart from increased alcohol tolerance for a few hours. It is believed that this fading was due to depletion of stem cells pools, which were then refilled using the protocols of the present protocols.

Alzheimer's Treatment:

A symmetric SC protocol may also be used in treatment of Alzheimer's disease (AD). The central cause of the disease is believed to derive from the buildup of plaques and the inflammation that results. But even when plaques are removed, memory problems can persist, and these can be ameliorated by the endogenous stimulation of NSCs. So an effective AD treatment can be divided into three parts: dissolving of plaques, detoxing of plaque debris, and restoration of memory by refilling neural stem cell pools damaged by Aβ toxicity and resulting inflammation.

In 2015, Kim et al. (PMID: 26646366) showed that Good's buffer 4-(2-Hydroxyethyl)-1-piperazinepropanesulfonic acid (HEPPS) produces disaggregation of amyloid-β (Aβ) plaques in mice genetically modified to overexpress Aβ. Cognitive ability was restored. In humans, AD also involves hyperphosphorylated tau (p-tau) which is sticky and combines extraneuronally with Aβ in plaques and forms intraneuronal neurofibrillary tangles. Aβ is upstream of p-tau in the pathogenesis of AD according to Bloom in 2014 (PMID: 24493463), and according to Jin et al. in 2011 (PMID: 21421841), Aβ directly leads to hyperphosphorylation of tau. But regardless of etiology, both must be addressed. In 2013 Liu et al., (PMID: 23273573) showed that nicotinamide reduced both Aβ and p-tau in genetically modified mice. Thus it was thought herein that combining nicotinamide and HEPPS would be especially effective.

As Aβ and p-tau released into the cerebrospinal fluid (CSF) will continue to be toxic and likely to redeposit, supplements known to be antioxidants capable of countering this toxicity were added to create a therapeutic cocktail. The volume of CFS is replaced at intervals of approximately six hours, and this can be taken as a half-life due to mixing by arterial pulsations. Thus the ideal antioxidants would be able to penetrate the BBB and demonstrate a half-life substantially greater than six hours, or alternatively, the antioxidants could be dosed at intervals.

Useful antioxidants comprise the amino acid taurine (which like HEPPS is a sulfonic acid), the olive oil polyphenols oleuropein aglycone and hydroxytyrosol, the flavonoid dihydromyricetin, vitamin C, and the primary cellular antioxidant, glutathione.

Taurine is found in large amounts in the brain and in energy drinks. In 2014, Kim et al. (PMID: 25502280) found that taurine can inhibit AP-related damage in genetically modified mice and recover cognitive ability. While taurine can produce some neural SC proliferation, this is improved with a fusion agent that can penetrate the BBB. Neural cells experience a unique nutritional environment due to the BBB, which excludes most saturated and mono-unsaturated fatty acids (such as palmitic, oleic, and stearic acids). Therefore sulforaphane is preferred as a mitochondrial fusion agent with this AD cocktail.

In 2011, Jazwa et al. (PMID: 21254817) showed that sulforaphane crossed the BBB of mice after intraperitoneal injection, with activity reaching a maximum in 15 minutes and lasting approximately sixty minutes. Sulforaphane is also known to be orally available, and oral dosing is preferred here. Sulforaphane or derivatives (sulforaphane glucosinolate) drive neural SC proliferation while also acting as an antioxidants, further protecting against toxic Aβ released by the cocktail.

Oleuropein aglycone is the major phenolic found in extra virgin olive oil. In August 2013, Grossi et al. (PMID: 23951225) found that oleuropein aglycone protected neurons from Aβ-induced cytotoxicity in transgenic mice. Hydroxytyrosol is a metabolite of oleuropein aglycone and is known to provide comparable neuroprotection to oleuropein aglycone in mice. In 2018, Feng et al. (PMID: 29869390) showed that dihydromyricetin inhibits microglial activation and neuroinflammation in AD mice. Carnosine is another common supplement useful here, which is known to suppress intraneuronal accumulation of Aβ, while also acting as an antioxidant and anti-glycative agent.

The following nutritional supplement cocktails—which evolved over time to include sulforaphane, but were otherwise substantially as shown here—were used for two individuals.

Examples of Alzheimer's Treatment Cocktails:
Plaque Cocktail, Part a (Dose):
  Taurine (10 g)
  HEPPS (1 g)
  Nicotinamide (500 mg)
  Carnosine (3 g)
Plaque Cocktail, Part B (Dose):
  Sulforaphane glucosinolate (50 mg)
  Oleuropein (100 mg)
  Hydroxytyrosol (25 mg)
  Dihydromyricetin (350 mg)
  Vitamin C (1 g)
  Glutathione, liposomal or phytosomal (500 mg)
Memory Cocktail (Dose):
  Sulforaphane glucosinolate (50 mg)
  Taurine (10 g)
  Methionine (2 g)
  TUDCA (250-500 mg)

Dosages are based on the male at about 85 kg and were reduced slightly for the lower weight of the female. Cocktail A was dosed in fruit juice and Cocktail B in tablets and capsules. They were taken together, with Cocktail B repeated after four hours. Cocktail C was added later and used separately.

Notes: Alcohol should not be used with TUDCA. Carnosine should be dosed at one gram or more to saturate the digestive enzyme carnosinase that destroys it, and HEPPS can be adjusted down to doses of 250 mg or less when first used, as the surge of released Aβ from loosely consolidated plaques can cause cognitive problems.

The first individual was male, 65 years old and had two APOE e4 genes. He had approximately 50 A/B treatments over 3 months. The second was female, 75 years old and has one APOE e4 gene, and has had some 20 A/B treatments over six months. Both were experiencing cognitive deficits that were substantially reversed by the treatments. Memory also improved after the addition the memory cocktail with sulforaphane.

Mitochondrial Aging:

Mitochondria are believed to be the descendants of ancient bacteria that pioneered oxidative chemistry. According to a popular hypothesis, at least once such bacterium was engulfed by an early eukaryotic cell to become an endosymbiont, and ultimately an organelle retaining its own DNA (mtDNA). Most of the original genes have been transferred to the nucleus, but human mtDNA still has 37 genes, all necessary for ATP production. If even one gene becomes mutated and nonfunctional, ATP productions stops. If a mitochondrion contains more than one loop and each loop has nonfunctional genes, then ATP production can continue if the defective genes are not the same on each loop. Thus two damaged loops of mtDNA can cover for each other, suppling enough RNA and polypeptides to maintain the pool of enzymes for ATP production and maintaining membrane potential ($\Delta\Psi m$). When $\Delta\Psi m$ drops sufficiently, a series of protein labels are applied, resulting in the defective mitochondrion being engulfed in a lysosome and enzymatically broken down and recycled. The constant fission and fusion of mitochondria serve to mix mtDNA and other components, and to occasionally reduce mitochondria to a minimal size containing one loop of mtDNA, allowing defective mitochondria to be detected and recycled via the well-known SIRT1-PINK1-Parkin pathway.

With aging, defective mitochondria build up faster than quality control can remove them, and certain drugs such as statins, psychotropics, acetaminophen, and others can cause mtDNA damage, sometimes so extensively that myopathy occurs. Damage to less than 100% of a cell's mtDNA can be reversed by artificially driving mitochondrial morphology into extreme fission and fusion cycles, along with supplements that support biogenesis of new mtDNA during fusion and support mitophagy during fission. This process is best performed prior to SC treatments, but can also be piggybacked on the SC protocol by adding a biogenesis promotor during mitochondrial fusion and a SIRT1 promoter during mitochondrial fission. As stem cells that divide asymmetrically segregate less functional mitochondria to the daughter cells, increasing mitophagy on occasion will rid new SC daughter cells of their initial load of dysfunctional mtDNA.

Biogenesis can be promoted by 10-50 mg of pyrroloquinoline quinone (PQQ), and SIRT1 by the high $NAD^+$/NADH ratio used with senolytics for apoptosis of senescent cells.

CONCLUSION

Aging is herein seen as an extended Hayflick crisis that can be treated by a protocol comprising repeated cycles of symmetric proliferation of endogenous stem cells that replenish stem cell pools quasi-exponentially, thus reducing the average epigenetic age of their resident tissues and the organism systemically as somatic cells are replaced naturally. Senolytic treatments then reduce the population of epigenetically old senescent cells that have become resistant to apoptosis, lowering the epigenetic age even further. Other sources and diseases of aging such as Alzheimer's and mitochondrial dysfunction can also be treated with the protocol, producing a comprehensive improvement in health and longevity.

The section headings used above are for organizational purposes only and are not to be construed as limiting. And although only a few exemplary embodiments of this invention have been described in detail, those skilled in the art will readily appreciate that many modifications are possible in the exemplary embodiments without materially departing from the novel teachings and advantages of this invention. Accordingly, all such modifications are intended to be included within the scope of this invention as defined in the following claims.

I claim:

1. A method for decreasing the epigenetic age of a mammalian organism having epigenetically old somatic cells and epigenetically young stem cells, comprising the steps:
   (a) endogenously stimulating mitochondria of said epigenetically young stem cells to a fusion state;
   (b) endogenously stimulating proliferation of at least a portion of said epigenetically young stem cells from step (a) into daughter stem cells; and
   (c) repeating steps (a) and (b) at least once after a delay for stem cell maturation.

2. The method as recited in claim 1, wherein step (a) comprises supplying a therapeutically effective oral dose of stearic acid and/or sulforaphane source.

3. The method as recited in claim 1, wherein step (b) comprises supplying a therapeutically effective dose of a UCP2 blocker.

4. The method as recited in claim 2, wherein step (b) comprises supplying a therapeutically effective dose of C60 dissolved in oil.

5. The method as recited in claim 1, wherein step (b) comprises delivering a therapeutically effective dose of nutrition to said epigenetically young stem cells.

6. The method as recited in claim 5, wherein said therapeutically effective dose of nutrition comprises methionine.

7. The method as recited in claim 6, wherein said therapeutically effective dose of nutrition further comprises leucine and lysine.

8. The method as recited in claim 1, further comprising:
   (d) stimulating apoptosis of at least a portion of epigenetically old somatic cells.

9. The method as recited in claim 8, wherein step (d) comprises supplying a therapeutically effective oral dose of a mitochondrial fission agent.

10. The method as recited in claim 8, wherein step (d) comprises dosing with a therapeutically effective amount of at least two from a group consisting of: apigenin, fisetin, curcumin, quercetin, resveratrol, dasatinib, navitoclax, piperlongumine, and a butyrate source.

11. The method as recited in claim 9, wherein said mitochondrial fission agent comprises an oxidized nicotinamide adenine dinucleotide ($NAD^+$) promoter, and/or apigenin.

12. The method as recited in claim 11, wherein the $NAD^+$ promoter is selected from one or more of a group consisting of: niacin; nicotinamide; nicotinamide riboside; nicotinamide and ribose; niacin and ribose; nicotinamide mononucleotide; and oxidized nicotinamide adenine dinucleotide.

* * * * *